United States Patent
Brunner et al.

(10) Patent No.: US 7,208,545 B1
(45) Date of Patent: Apr. 24, 2007

(54) SELECTED CYCLOHEXANE -1,3-AND -1,4-DICARBOXYLIC ACID ESTERS

(75) Inventors: Melanie Brunner, Mannheim (DE); Lucien Thil, Limburgerhof (DE); Boris Breitscheidel, Limburgerhof (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/959,380

(22) PCT Filed: Jun. 9, 2000

(86) PCT No.: PCT/EP00/05351

§ 371 (c)(1),
(2), (4) Date: Oct. 24, 2001

(87) PCT Pub. No.: WO00/78704

PCT Pub. Date: Dec. 28, 2000

(30) Foreign Application Priority Data

Jun. 18, 1999 (DE) ................... 199 27 978

(51) Int. Cl.
*C08K 5/12* (2006.01)
*C07C 69/74* (2006.01)

(52) U.S. Cl. ........................ 524/569; 560/127
(58) Field of Classification Search ................ 560/127
See application file for complete search history.

(56) References Cited

U.S. PATENT DOCUMENTS

| | | | |
|---|---|---|---|
| 3,027,398 A | 3/1962 | Foohey | 260/468 |
| 3,308,086 A | 3/1967 | Wartman | 260/30 |
| 5,286,898 A | 2/1994 | Gustafson et al. | 560/127 |
| 5,319,129 A | 6/1994 | Gustafson et al. | 560/127 |
| 6,284,917 B1 | 9/2001 | Brunner et al. | 560/127 |

FOREIGN PATENT DOCUMENTS

| | | | |
|---|---|---|---|
| DE | 1 263 296 | | 3/1968 |
| DE | 28 23 165 | | 11/1979 |
| EP | 0 603 825 | | 6/1994 |
| FR | 2397131 | | 3/1979 |
| JP | 07011074 | | 1/1995 |
| JP | 09-181306 | * | 2/1999 |
| WO | WO 97/21792 | | 6/1997 |
| WO | WO 9721792 | * | 9/1997 |
| WO | WO 99/32427 | | 7/1999 |

OTHER PUBLICATIONS

CA 57: 12711a : Matsuda et al, Cyclohexanes carboxylates for use as Plasticizers.*
Matsuda et al, as disclosed in CA 57: 12711 (1959).*
Matsuda et al, as disclosed in CA 57: 12711 (1959).*
CA 127:515741, Kawahara et al citation for WO 9721792 cited above.*

* cited by examiner

*Primary Examiner*—Paul A. Zucker
(74) *Attorney, Agent, or Firm*—Novak Druce & Quigg LLP

(57) ABSTRACT

Selected cyclohexane-1,3- and -1,4-dicarboxylic acid esters are described, as is their use as plasticizers in plastics and their preparation by hydrogenation of the corresponding isophthalic or terephthalic esters by bringing one or more of these isophthalic or terephthalic esters into contact with a hydrogen-containing gas in the presence of a catalyst which comprises, as active metal, at least one metal of the 8th transition group of the Periodic Table on its own or together with at least one metal of the 1st or 7th transition group of the Periodic Table, applied to a support, which comprises using a support having micropores.

25 Claims, No Drawings

SELECTED CYCLOHEXANE -1,3-AND -1,4-DICARBOXYLIC ACID ESTERS

The invention relates to selected cyclohexane-1,3- and -1,4-dicarboxylic acid esters, their use as plasticizers in plastics, and also their preparation by hydrogenating the corresponding isophthalic or terephthalic esters, by bringing one or more of these isophthalic or terephthalic esters into contact with a hydrogen-containing gas in the presence of a catalyst having macropores.

The plasticizers used hitherto in plastics, e.g. PVC, have very often been phthalates, e.g. dibutyl, dioctyl or diisononyl phthalates, as can be found, for example, in FR-A 23 97 131. However, these have been recently said to give concerns on health grounds, and their use in plastics for producing children's toys, for example, is therefore increasingly under criticism and in many countries already forbidden. Animal experiments have now shown that phthalates can cause peroxisome proliferation, which has a causal connection with liver tumors found in long-term studies on mice and rats.

The use of some cyclohexane-1,2-dicarboxylic acid esters as plasticizers is likewise known from the prior art. For example, the use of cyclohexanedicarboxylic acid dimethyl or diethyl esters (DE-A 28 23 165), and also of cyclohexane-1,2-dicarboxylic acid di(2-ethyl-hexyl) ester (DE-A 12 63 296) as plasticizers in plastics is described.

PCT/EP 98/08346 relates inter alia to the use of cyclohexanepolycarboxylic acid esters as plasticizers in plastics, and also to selected new cyclohexane-1,2-dicarboxylic acid esters. No new cyclohexane-1,3- or -1,4-dicarboxylic acid derivatives are disclosed in PCT/EP 98/08346. There is also absolutely no mention of the toxicological properties of cyclohexanepolycarboxylic acids or derivatives of these in PCT/EP 98/08346.

It is an object of the invention, therefore, to provide novel cyclohexane-1,3- and -1,4-dicarboxylic acid derivatives, in particular derivatives which are suitable for use as plasticizers in plastic, and also the use of these as plasticizers in plastics. A further object of the present invention is to provide, for use as plasticizers in plastics, novel cyclohexane-1,3- and -1,4-dicarboxylic acid derivatives which are suitable on the basis of their physical and material properties for use as plasticizers in plastics and are also regarded as suitable for use as plasticizers in plastics on the basis of their toxicological properties. A further object of the present invention is to provide a process for preparing the novel cyclohexane-1,3- and -1,4-dicarboxylic acid derivatives, allowing these compounds to be obtained with very high selectivity and space-time yield and without any significant side reactions.

U.S. Pat. No. 5,286,898 and U.S. Pat. No. 5,319,129 hydrogenate dimethyl terephthalate on supported Pd catalysts mixed with Ni, Pt and/or Ru at or above 140° C. at a pressure of from 50 to 170 bar, to give the corresponding dimethyl hexahydroterephthalate. DE-A 28 23 165 hydrogenates aromatic carboxylic esters on catalysts comprising supported Ni, Ru, Rh and/or Pd, to give the corresponding cycloaliphatic carboxylic esters, at from 70 to 250° C. and at from 30 to 200 bar. U.S. Pat. No. 3,027,398 describes the hydrogenation of dimethyl terephthalate on supported Ru catalysts at from 110 to 140° C. and from 35 to 105 bar.

EP-A 0 603 825 relates to a process for producing 1,4-cyclohexanedicarboxylic acid by hydrogenating terephthalic acid, using a supported palladium catalyst, where the support used comprises aluminum oxide, silicon dioxide or activated carbon. The process which it describes is in particular characterized by bringing the solution obtained in a first step and comprising 1,4-cyclohexanedicarboxylic acid into contact with steam, thereby extracting contaminants present in this solution. However, this process is applicable only to acids, since there is a risk of hydrolysis when it is applied to derivatives, such as esters, anhydrides, etc. Said application makes absolutely no mention of any use of a support having macropores.

The application PCT/EP 98/08346 mentioned above discloses a process for hydrogenating benzenepolycarboxylic acid or derivatives thereof, e.g. esters and/or anhydrides, by bringing one or more benzenepolycarboxylic acids, or one or more derivatives thereof, into contact with a hydrogen-containing gas in the presence of a catalyst having macropores.

We have found that the object of the present invention is achieved by providing selected cyclohexane-1,3- and -1,4-dicarboxylic acid esters, in particular esters which are suitable for use as plasticizers in plastic. The invention also provides their use as plasticizers in plastics and the preparation of these selected cyclohexane-1,3- and -1,4-dicarboxylic acid esters by hydrogenating the corresponding isophthalic or terephthalic esters, or hydrogenating a mixture made from two or more of these, by bringing one or more of the corresponding isophthalic or terephthalic esters into contact with a hydrogen-containing gas in the presence of a catalyst having macropores.

In particular, the present invention provides the following cyclohexane-1,3- or -1,4-dicarboxylic acid esters (cf. Tables 1 and 2):

Cyclohexane-1,3-dicarboxylic acid diisobutyl ester obtainable by hydrogenating diisobutyl isophthalate with Chemical Abstracts Registry number (hereinafter: CAS No.) 1528-64-9;

Cyclohexane-1,3-dicarboxylic acid dipentyl ester obtainable by hydrogenating dipentyl isophthalate with CAS No. 4654-16-4;

Cyclohexane-1,3-dicarboxylic acid bis(1-methylbutyl) ester obtainable by hydrogenating bis(1-methylbutyl) isophthalate with CAS No. 75151-01-8;

Cyclohexane-1,3-dicarboxylic acid diheptyl ester obtainable by hydrogenating diheptyl isophthalate with CAS No. 4654-17-5;

Cyclohexane-1,3-dicarboxylic acid diisooctyl ester obtainable by hydrogenating diisooctyl isophthalate with CAS No. 71850-11-8;

Cyclohexane-1,3-dicarboxylic acid dinonyl ester obtainable by hydrogenating dinonyl isophthalate with CAS No. 4654-19-7;

Cyclohexane-1,3-dicarboxylic acid diisodecyl ester obtainable by hydrogenating diisodecyl isophthalate with CAS No. 52284-35-2;

Cyclohexane-1,3-dicarboxylic acid diundecyl ester obtainable by hydrogenating diundecyl isophthalate with CAS No. 18699-46-2;

Cyclohexane-1,3-dicarboxylic acid didodecyl ester obtainable by hydrogenating didodecyl isophthalate with CAS No. 18699-47-3;

Cyclohexane-1,3-dicarboxylic acid bis(1-methylpropyl) ester obtainable by hydrogenating bis(1-methylpropyl) isophthalate with CAS No. 75150-99-1;

Cyclohexane-1,3-dicarboxylic acid bis(1,1-dimethylpropyl) ester obtainable by hydrogenating bis(1,1-dimethylpropyl) isophthalate with CAS No. 117769-95-6;

Cyclohexane-1,3-dicarboxylic acid bis(2-methylbutyl) ester obtainable by hydrogenating bis(2-methylbutyl) isophthalate with CAS No. 75151-03-0;

Cyclohexane-1,3-dicarboxylic acid bis(3-methylbutyl) ester obtainable by hydrogenating bis(3-methylbutyl) isophthalate with CAS No. 1528-63-8;

Cyclohexane-1,3-dicarboxylic acid bis(1-ethyl-2-methylpropyl) ester obtainable by hydrogenating bis(1-ethyl-2-methylpropyl) isophthalate with CAS No. 166391-29-3;

Cyclohexane-1,3-dicarboxylic acid bis(1-ethylbutyl) ester obtainable by hydrogenating bis(1-ethylbutyl) isophthalate with CAS No. 166391-28-2;

Cyclohexane-1,3-dicarboxylic acid bis(1,2,2-trimethylpropyl) ester obtainable by hydrogenating bis(1,2,2-trimethylpropyl) isophthalate with CAS No. 166391-27-1;

Cyclohexane-1,3-dicarboxylic acid bis(2-ethylbutyl) ester obtainable by hydrogenating bis(2-ethylbutyl) isophthalate with CAS No. 166391-25-9;

Cyclohexane-1,3-dicarboxylic acid bis(4-methylpentyl) ester obtainable by hydrogenating bis(4-methylpentyl) isophthalate with CAS No. 159375-22-1;

Cyclohexane-1,3-dicarboxylic acid bis(1,3-dimethylbutyl) ester obtainable by hydrogenating bis(1,3-dimethylbutyl) isophthalate with CAS No. 166391-26-0;

Cyclohexane-1,3-dicarboxylic acid bis(1,1-diethylpropyl) ester obtainable by hydrogenating bis(1,1-diethylpropyl) isophthalate with CAS No. 123095-15-8;

Cyclohexane-1,3-dicarboxylic acid bis(1-ethyl-1-methylpropyl) ester obtainable by hydrogenating bis(1-ethyl-1-methylpropyl) isophthalate with CAS No. 145530-74-1;

Cyclohexane-1,3-dicarboxylic acid bis[2-methyl-1-(1-methylethyl)propyl] ester obtainable by hydrogenating bis[2-methyl-1-(1-methylethyl)propyl] isophthalate with CAS No. 166391-48-6;

Cyclohexane-1,3-dicarboxylic acid bis(2,2-dimethylhexyl) ester obtainable by hydrogenating bis(2,2-dimethylhexyl) isophthalate with CAS No. 17673-11-9;

Cyclohexane-1,3-dicarboxylic acid bis[3-methyl-1-(2-methylpropyl)butyl] ester obtainable by hydrogenating bis[3-methyl-1-(2-methylpropyl)butyl] isophthalate with CAS No. 127474-92-4;

Cyclohexane-1,3-dicarboxylic acid bis(3,3,5-trimethylhexyl) ester obtainable by hydrogenating bis(3,3,5-trimethylhexyl) isophthalate with CAS No. 208527-97-3;

Cyclohexane-1,3-dicarboxylic acid bis(2-ethyl-1,1-dimethylhexyl) ester obtainable by hydrogenating bis(2-ethyl-1,1-dimethylhexyl) isophthalate with CAS No. 123892-24-0;

Cyclohexanedicarboxylic acid 1-heptyl-3-hexyl ester obtainable by hydrogenating 1-heptyl-3-hexyl isophthalate with CAS No. 166391-30-6;

Cyclohexanedicarboxylic acid 1-[2-ethylbutyl]-3-heptyl ester obtainable by hydrogenating 1-[2-ethylbutyl]-3-heptyl isophthalate with CAS No. 166391-41-9;

Cyclohexanedicarboxylic acid 1-heptyl-3-[1,2,2-trimethylpropyl] ester obtainable by hydrogenating 1-heptyl-3-[1,2,2-trimethylpropyl] isophthalate with CAS No. 166391-43-1;

Cyclohexanedicarboxylic acid 1-dimethylbutyl-3-heptyl ester obtainable by hydrogenating 1-dimethylbutyl-3-heptyl isophthalate with CAS No. 166391-42-0;

Cyclohexanedicarboxylic acid 1-[1-ethylbutyl]-3-heptyl ester obtainable by hydrogenating 1-[1-ethylbutyl]-3-heptyl isophthalate with CAS No. 166391-44-2;

Cyclohexanedicarboxylic acid 1-[1-ethyl-2-methylpropyl]-3-heptyl ester obtainable by hydrogenating 1-[1-ethyl-2-methylpropyl]-3-heptyl isophthalate with CAS No. 166391-45-3;

Cyclohexanedicarboxylic acid 1-decyl-3-hexyl ester obtainable by hydrogenating 1-decyl-3-hexyl isophthalate with CAS No. 154064-19-4;

Cyclohexanedicarboxylic acid 1-hexyl-3-[2-methyl-1-(1-methylethyl)propyl] ester obtainable by hydrogenating 1-hexyl-3-[2-methyl-1-(1-methylethyl)propyl] isophthalate with CAS No. 166391-46-4;

Cyclohexanedicarboxylic acid 1-dodecyl-3-hexyl ester obtainable by hydrogenating 1-dodecyl-3-hexyl isophthalate with CAS No. 154147-75-8;

Cyclohexanedicarboxylic acid 1-nonyl-3-octyl ester obtainable by hydrogenating 1-nonyl-3-octyl isophthalate with CAS No. 154147-74-7;

Cyclohexane-1,4-dicarboxylic acid diisobutyl ester obtainable by hydrogenating diisobutyl terephthalate with Chemical Abstracts Registry number (hereinafter: CAS No.) 18699-48-4;

Cyclohexane-1,4-dicarboxylic acid dipentyl ester obtainable by hydrogenating dipentyl terephthalate with CAS No. 1818-95-7;

Cyclohexane-1,4-dicarboxylic acid bis(1-methylbutyl) ester obtainable by hydrogenating bis(1-methylbutyl) terephthalate with CAS No. 75151-02-9;

Cyclohexane-1,4-dicarboxylic acid diheptyl ester obtainable by hydrogenating diheptyl terephthalate with CAS No. 4654-25-5;

Cyclohexane-1,4-dicarboxylic acid diisooctyl ester obtainable by hydrogenating diisooctyl terephthalate with CAS No. 27937-24-2;

Cyclohexane-1,4-dicarboxylic acid dinonyl ester obtainable by hydrogenating dinonyl terephthalate with CAS No. 4654-27-7;

Cyclohexane-1,4-dicarboxylic acid diisononyl ester obtainable by hydrogenating diisononyl terephthalate with CAS No. 59802-05-0;

Cyclohexane-1,4-dicarboxylic acid diisodecyl ester obtainable by hydrogenating diisodecyl terephthalate with CAS No. 52174-72-8;

Cyclohexane-1,4-dicarboxylic acid diundecyl ester obtainable by hydrogenating diundecyl terephthalate with CAS No. 111204-04-7;

Cyclohexane-1,4-dicarboxylic acid didodecyl ester obtainable by hydrogenating didodecyl terephthalate with CAS No. 18749-84-3;

Cyclohexane-1,4-dicarboxylic acid bis(1-methylpropyl) ester obtainable by hydrogenating bis(1-methylpropyl) terephthalate with CAS No. 64445-74-5;

Cyclohexane-1,4-dicarboxylic acid bis(1,1-dimethylpropyl) ester obtainable by hydrogenating bis(1,1-dimethylpropyl) terephthalate with CAS No. 117769-96-7;

Cyclohexane-1,4-dicarboxylic acid bis(2-methylbutyl) ester obtainable by hydrogenating bis(2-methylbutyl) terephthalate with CAS No. 75151-04-1;

Cyclohexane-1,4-dicarboxylic acid bis(3-methylbutyl) ester obtainable by hydrogenating bis(3-methylbutyl) terephthalate with CAS No. 18699-49-5;

Cyclohexane-1,4-dicarboxylic acid bis(1-ethylbutyl) ester obtainable by hydrogenating bis(1-ethylbutyl) terephthalate with CAS No. 166391-32-8;

Cyclohexane-1,4-dicarboxylic acid bis(4-methylpentyl) ester obtainable by hydrogenating bis(4-methylpentyl) terephthalate with CAS No. 159375-21-0;

Cyclohexane-1,4-dicarboxylic acid bis[2-methyl-1-(1-methylethyl)propyl] ester obtainable by hydrogenating bis[2-methyl-1-(1-methylethyl)propyl] terephthalate with CAS No. 166391-33-9;

2-Methylcyclohexane-1,4-dicarboxylic acid bis(2-ethylhexyl) ester obtainable by hydrogenating bis(2-ethylhexyl) 2-methylterephthalate with CAS No. 51248-91-0;

Cyclohexane-1,4-dicarboxylic acid bis(1-methylheptyl) ester obtainable by hydrogenating bis(1-methylheptyl) terephthalate with CAS No. 87321-19-5;

Cyclohexane-1,4-dicarboxylic acid bis(2-ethyl-4-methylpentyl) ester obtainable by hydrogenating bis(2-ethyl-4-methylpentyl) terephthalate with CAS No. 59726-62-4;

Cyclohexane-1,4-dicarboxylic acid bis(2-methylheptyl) ester obtainable by hydrogenating bis(2-methylheptyl) terephthalate with CAS No. 83789-07-5;

Cyclohexane-1,4-dicarboxylic acid bis(1,1,3,3-tetramethylbutyl) ester obtainable by hydrogenating bis(1,1,3,3-tetramethylbutyl) terephthalate with CAS No. 90062-57-0;

Cyclohexane-1,4-dicarboxylic acid bis(7-methyloctyl) ester obtainable by hydrogenating bis(7-methyloctyl) terephthalate with CAS No. 129951-42-4;

Cyclohexane-1,4-dicarboxylic acid bis(8-methylnonyl) ester obtainable by hydrogenating bis(8-methylnonyl) terephthalate with CAS No. 129951-40-2;

Cyclohexanedicarboxylic acid 1-[8-methylnonyl]-4-octyl ester obtainable by hydrogenating 1-[8-methylnonyl]-4-octyl terephthalate with CAS No. 129951-39-9;

Cyclohexanedicarboxylic acid 1-decyl-4-octyl ester obtainable by hydrogenating 1-decyl-4-octyl terephthalate with CAS No. 129951-41-3.

The present invention further provides a process for preparing the novel cyclohexane-1,3- and -1,4-dicarboxylic acid derivatives or preparing a mixture made from two or more of these by hydrogenation of the corresponding isophthalic or terephthalic acid derivatives, by bringing the corresponding isophthalic or terephthalic acid derivative, or the mixture made from two or more of these, into contact with a hydrogen-containing gas in the presence of a catalyst which comprises, as active metal, at least one metal of the 8$^{th}$ transition group of the Periodic Table on its own or together with at least one metal of the 1$^{st}$ or 7$^{th}$ transition group of the Periodic Table, applied to a support, which comprises using a support having macropores.

In a preferred embodiment the present invention provides a process for the hydrogenation of the isophthalic or terephthalic ester of a mixture made from two or more of these where the catalyst comprises, as active metal, at least one metal of the 8$^{th}$ transition group of the Periodic Table on its own or together with at least one metal of the 1$^{st}$ or 7$^{th}$ transition group of the Periodic Table, applied to a support, where the support has an average pore diameter of at least 50 nm and a BET surface area of not more than 30 m$^2$/g and the amount of the active metal is from 0.01 to 30% by weight, based on the total weight of the catalyst (catalyst 1).

The invention further provides a process of this type where the catalyst comprises, as active metal, from 0.01 to 30% by weight, based on the total weight of the catalyst, of at least one metal of the 8$^{th}$ transition group of the Periodic Table on its own or together with at least one metal of the 1$^{st}$ or 7$^{th}$ transition group of the Periodic Table, applied to a support, where from 10 to 50% of the pore volume of the support is formed by macropores with a pore diameter of from 50 to 10,000 nm and from 50 to 90% of the pore volume of the support is formed by mesopores with a pore diameter of from 2 to 50 nm, where the pore volume proportions give 100% in total (catalyst 2).

In another preferred embodiment, the present invention provides a process as defined above where the catalyst (catalyst 3) comprises, as active metal, from 0.01 to 30% by weight, based on the total weight of the catalyst, of at least one metal of the 8$^{th}$ transition group of the Periodic Table on its own or together with at least one metal of the 1$^{st}$ or 7$^{th}$ transition group of the Periodic Table, applied to a support, where the support has an average pore diameter of at least 0.1 μm and a BET surface area of not more than 15 m$^2$/g. The support used may in principle be any support which has macropores, i.e. any support which has exclusively macropores or any support which has macropores and meso- and/or micropores.

The active metal used may in principle be any of the metals of the 8$^{th}$ transition group of the Periodic Table. It is preferable for the active metals used to be platinum, rhodium, palladium, cobalt, nickel or ruthenium, or a mixture made from two or more of these, and ruthenium is in particular used as active metal. Among the metals of the 1$^{st}$ or 7$^{th}$, or the 1$^{st}$ and the 7$^{th}$, transition group of the Periodic Table which can also be used, preference is given to the use of copper and/or rhenium, but in principle any of these metals may be used.

For the purposes of the present invention the definitions of the terms "macropores" and "mesopores" are those given in *Pure Appl. Chem.* 45 p. 79 (1976), i.e. pores whose diameter is above 50 nm (macropores) or from 2 to 50 nm (mesopores).

The content of the active metal is generally from about 0.01 to about 30% by weight, preferably from about 0.01 to about 5% by weight and in particular from about 0.05 to about 5% by weight, based in each case on the total weight of the catalyst used. For catalysts 1 to 3 described below, whose use is preferred, the preferred content used is again stated separately during the discussion of these catalysts.

The catalysts 1 to 3, whose use is preferred, will now be described below in greater detail. The description here takes as an example the use of ruthenium as active metal. However, statements made below are equally applicable to the other active metals which may be used, as defined herein.

Catalyst 1

The catalysts 1 which are used according to the invention may be prepared industrially by applying at least one metal of the 8$^{th}$ transition group of the Periodic Table, and, if desired, at least one metal of the 1$^{st}$ or 7$^{th}$ transition group of the Periodic Table, to a suitable support.

It may be applied by saturating the support in aqueous metal salt solutions, e.g. in aqueous ruthenium salt solutions, by spray-application of appropriate metal salt solutions to the support, or by other suitable processes. Suitable metal salts of the 1$^{st}$, 7$^{th}$ or 8$^{th}$ transition group of the Periodic Table are the nitrates, nitrosyl nitrates, halides, carbonates, carboxylates, acetylacetonates, chloro complexes, nitrito complexes or amine complexes of the appropriate metals, preferably the nitrates and nitrosyl nitrates.

In the case of catalysts which, besides the metal of the 8$^{th}$ transition group of the Periodic Table, also comprise other metals as active metal applied to the support. The metal salts and/or metal salt solutions may be applied simultaneously or in succession.

The supports coated or saturated with the metal salt solution are then dried, preferably at from 100 to 150° C. and, if desired, calcined at from 200 to 600° C., preferably from 350 to 450° C. In the case of separate saturation, the catalyst is dried and, if desired, calcined, as described above, after each saturation step. The sequence in which the active components are applied by saturation here may be as desired.

The coated and dried and also, if desired, calcined supports are then activated by treatment in a stream of gas which comprises free hydrogen, at from about 30 to about 600° C., preferably from about 150 to about 450° C. The stream of gas is preferably composed of from 50 to 100% by volume of $H_2$ and from 0 to 50% by volume of $N_2$.

The amounts of the metal salt solution(s) applied to the support(s) are such that the total content of active metal, based in each case on the total weight of the catalyst, is from about 0.01 to about 30% by weight, preferably from about 0.01 to about 5% by weight, more preferably from about 0.01 to about 1% by weight, and in particular from about 0.05 to about 1% by weight.

The total metal surface area on the catalyst 1 is preferably from about 0.01 to about 10 $m^2/g$ of catalyst, more preferably from about 0.05 to about 5 $m^2/g$ of catalyst and in particular from about 0.05 to about 3 $m^2/g$ of catalyst. The metal surface area is determined by the chemisorption method described by J. Lemaitre et al. in "*Characterization of Heterogeneous Catalysts*", ed. Francis Delanney, Marcel Dekker, New York 1984, pp. 310–324.

In the catalyst 1 used according to the invention the ratio of the surface areas of the active metal(s) and of the catalyst support is preferably less than about 0.05, and the lower limit is about 0.0005.

The support materials which may be used to prepare the catalysts used according to the invention are those which are macroporous and have an average pore diameter of at least about 50 nm, preferably at least about 100 nm, in particular at least about 500 nm, and whose BET surface area is not more than about 30 $m^2/g$, preferably not more than about 15 $m^2/g$, more preferably not more than about 10 $m^2/g$, in particular not more than about 5 $m^2/g$, and still more preferably not more than about 3 $m^2/g$. The average pore diameter of the support is preferably from about 100 nm to about 200 μm, more preferably from about 500 nm to about 50 μm. The surface area of the support is preferably from about 0.2 to about 15 $m^2/g$, more preferably from about 0.5 to about 10 $m^2/g$, in particular from about 0.5 to about 5 $m^2/g$ and still more preferably from about 0.5 to about 3 $m^2/g$.

The surface area of the support is determined by the BET method by $N_2$ adsorption, in particular to DIN 66131. The average pore diameter and the pore size distribution are determined by Hg porosimetry, in particular to DIN 66133.

The pore size distribution of the support may preferably be approximately bimodal, the pore diameter distribution having maxima at about 600 nm and about 20 μm in the bimodal distribution in a specific embodiment of the invention.

The support more preferably has a surface area of 1.75 $m^2/g$ and a bimodal distribution of pore diameter. The pore volume of this preferred support is preferably about 0.53 ml/g.

Examples of macroporous support materials which may be used are macroporous activated carbon, silicon carbide, aluminum oxide, silicon dioxide, titanium dioxide, zirconium dioxide, magnesium oxide, zinc oxide and mixtures made from two or more of these, preferably aluminum oxide or zirconium dioxide.

Further details concerning catalyst 1 and its preparation may be found in DE-A 196 24 484.6, the entire relevant content of which is incorporated into the present application by way of reference.

Catalyst 2

The catalysts 2 used according to the invention comprise one or more metals of the $8^{th}$ transition group of the Periodic Table as active component(s) on a support, as defined herein. Preference is given to using ruthenium, palladium and/or rhodium as active component(s).

The catalysts 2 which are used according to the invention may be prepared industrially by applying at least one active metal of the $8^{th}$ transition group of the Periodic Table, preferably ruthenium or palladium, and, if desired, at least one metal of the $1^{st}$ or $7^{th}$ transition group of the Periodic Table, to a suitable support. It may be applied by saturating the support in aqueous metal salt solutions, e.g. in ruthenium salt solutions or palladium salt solutions, by spray-application of appropriate metal salt solutions to the support, or by other suitable processes. Suitable metal salts for the preparation of metal salt solutions are the nitrates, nitrosyl nitrates, halides, carbonates, carboxylates, acetylacetonates, chloro complexes, nitrito complexes or amine complexes of the appropriate metals, preferably the nitrates and nitrosyl nitrates.

In the case of catalysts which comprise two or more active metals applied to the support, the metal salts and/or metal salt solutions may be applied simultaneously or in succession.

The supports coated or saturated with the metal salt solution are then dried, preferably at from 100 to 150° C. If desired, these supports may be calcined at from 200 to 600° C., preferably from 350 to 450° C. The coated supports are then activated by treatment in a stream of gas which comprises free hydrogen, at from 30 to 600° C., preferably from 100 to 450° C. and in particular from 100 to 300° C. The stream of gas is preferably composed of from 50 to 100% by volume of $H_2$ and from 0 to 50% by volume of $N_2$.

If two or more active metals are applied to the supports and if the application takes place in succession, the support may be dried after each application or saturation at from 100 to 150° C. and, if desired, calcined at from 200 to 600° C. The sequence in which the metal salt solutions are applied here, by saturation or otherwise, may be as desired.

The amount of the metal salt solution applied to the support(s) is such that the content of active metal, based on the total weight of the catalyst, is from 0.01 to 30% by weight, preferably from 0.01 to 10% by weight, more preferably from 0.01 to 5% by weight, and in particular from 0.3 to 1% by weight.

The total metal surface area on the catalyst is preferably from 0.01 to 10 $m^2/g$ of catalyst, more preferably from 0.05 to 5 $m^2/g$ of catalyst and in particular from 0.05 to 3 $m^2/g$ of catalyst. The metal surface area was determined by the chemisorption method described by J. Lemaitre et al. in "*Characterization of Heterogeneous Catalysts*", ed. Francis Delanney, Marcel Dekker, New York 1984, pp. 310–324.

In the catalyst 2 used according to the invention the ratio of the surface areas of the at least one active metal and of the catalyst support is less than about 0.3, preferably less than about 0.1 and in particular about 0.05 or less, and the lower limit is about 0.0005.

The support materials which can be used to prepare the catalysts 2 used according to the invention have macropores and mesopores.

The supports which can be used here according to the invention have a pore distribution in which from about 5 to about 50%, preferably from about 10 to about 45%, more preferably from about 10 to about 30% and in particular from about 15 to about 25%, of the pore volume has been formed by macropores with pore diameters of from about 50 nm to about 10,000 nm, and from about 50 to about 95%, preferably from about 55 to about 90%, more preferably from about 70 to about 90% and in particular from about 75 to about 85% of the pore volume has been formed by mesopores with a pore diameter of from about 2 to about 50 nm, where in each case the pore volume proportions give 100% in total.

The total pore volume of the support used according to the invention is from about 0.05 to 1.5 cm³/g, preferably from 0.1 to 1.2 cm³/g and in particular from about 0.3 to 1.0 cm³/g. The average pore diameter of the support used according to the invention is from about 5 to 20 nm, preferably from about 8 to about 15 nm and in particular from about 9 to about 12 nm.

The surface area of the support is preferably from about 50 to about 500 m²/g of the support, more preferably from about 200 to about 350 m²/g of the support and in particular from about 250 to about 300 m²/g of the support.

The surface area of the support is determined by the BET method by $N_2$ adsorption, in particular to DIN 66131. The average pore diameter and the size distribution are determined by Hg porosimetry, in particular to DIN 66133.

Although in principle use may be made of any support materials known for catalyst preparation, i.e. those which have the pore size distribution defined above, it is preferable to use macroporous activated carbon, silicon carbide, aluminum oxide, silicon dioxide, titanium dioxide, zirconium dioxide, magnesium oxide, zinc oxide or mixtures of these, more preferably aluminum oxide or zirconium dioxide.

Further details concerning catalyst 2 and its preparation may be found in DE-A 196 24 485.4, the entire relevant content of which is incorporated into the present application by way of reference.

Catalyst 3

The catalysts 3 which are used according to the invention may be prepared industrially by applying an active metal of the $8^{th}$ transition group of the Periodic Table, and, if desired, at least one metal of the $1^{st}$ or $7^{th}$ transition group of the Periodic Table, to a suitable support. It may be applied by saturating the support in aqueous metal salt solutions, e.g. in ruthenium salt solutions, by spray-application of appropriate metal salt solutions to the support, or by other suitable processes. Suitable ruthenium salts for preparing the ruthenium salt solutions, or suitable metal salts of the $1^{st}$, $7^{th}$ or $8^{th}$ transition group, are the nitrates, nitrosyl nitrates, halides, carbonates, carboxylates, acetylacetonates, chloro complexes, nitrito complexes or amine complexes of the appropriate metals, preferably the nitrates and nitrosyl nitrates.

In the case of catalysts which comprise two or more metals applied to the support, the metal salts and/or metal salt solutions may be applied simultaneously or in succession.

The supports coated with ruthenium salt solution or with metal salt solution, or the saturated supports, are then dried, preferably at from 100 to 150° C., and, if desired, calcined at from 200 to 600° C.

The coated supports are then activated by treating the coated supports in a stream of gas which comprises free hydrogen, at from 30 to 600° C., preferably from 150 to 450° C. The stream of gas is preferably composed of from 50 to 100% by volume of $H_2$ and from 0 to 50% by volume of $N_2$.

If metals of the $1^{st}$ or $7^{th}$ transition group are applied to the supports, besides the active metal of the $8^{th}$ transition group of the Periodic Table, and if the application takes place in succession, the support may be dried after each application or saturation at from 100 to 150° C. and, if desired, calcined at from 200 to 600° C. The sequence in which the metal salt solutions are applied here, by saturation or otherwise, may be as desired.

The amount of the metal salt solution applied to the support(s) is such as to give from 0.01 to 30% by weight of active metal, based on the total weight of the catalyst, on the support. This amount is preferably from 0.2 to 15% by weight, particularly preferably about 0.5% by weight.

The total metal surface area on the catalyst 3 is preferably from 0.01 to 10 m²/g of the catalyst, particularly preferably from 0.05 to 5 m²/g of the catalyst, in particular from 0.05 to 3 m²/g of the catalyst.

The support materials which may be used to prepare the catalysts 3 used according to the invention are preferably those which are macroporous and have an average pore diameter of at least 0.1 μm, preferably at least 0.5 μm, and a surface area of not more than 15 m²/g, preferably not more than 10 m²/g, particularly preferably not more than 5 m²/g, in particular not more than 3 m²/g. The average pore diameter of the support is preferably from 0.1 to 200 μm, in particular from 0.5 to 50 μm. The surface area of the support is preferably from 0.2 to 15 m²/g of the support, particularly preferably from 0.5 to 10 m²/g of the support, in particular from 0.5 to 5 m²/g of the support, specifically from 0.5 to 3 m²/g of the support.

The surface area of the support is determined by the BET method by $N_2$ adsorption, in particular to DIN 66131. The average pore diameter and the pore size distribution were determined by Hg porosimetry, in particular to DIN 66133. The pore size distribution of the support may preferably be approximately bimodal, the pore diameter distribution having maxima at about 0.6 μm and about 20 μm in the bimodal distribution in a specific embodiment of the invention.

It is particularly preferable for a support to have a surface area of about 1.75 m²/g and this bimodal distribution of the pore diameter. The pore volume of this preferred support is preferably about 0.53 ml/g.

Examples of macroporous support materials which may be used are macroporous activated carbon, silicon carbide, aluminum oxide, silicon dioxide, titanium dioxide, zirconium dioxide, magnesium oxide, zinc oxide or mixtures of these, preferably aluminum oxide or zirconium dioxide.

Further details concerning catalyst 3 and its preparation may be found in DE-A 196 04 791.9, the entire relevant content of which is incorporated into the present application by way of reference.

Conduct of the Process

For the purposes of the novel process the hydrogenation is generally carried out at from about 50 to 250° C., preferably from about 70 to 220° C. The pressures used for the process are generally above 10 bar, preferably from about 20 to about 300 bar.

The novel process may be carried out either continuously or batchwise, preferably continuously.

In the continuous conduct of the process the amount of the benzenedicarboxylic ester(s) intended for hydrogenation, or of the mixture made from two or more of these, is preferably from about 0.05 to about 3 kg per liter of catalyst per hour, more preferably from about 0.1 to about 1 kg per liter of catalyst per hour.

Hydrogenation gases which may be used are any desired gases which comprise free hydrogen and do not have injurious amounts of catalyst poisons, such as CO. Use may be made, for example, of waste gases from a reformer. It is preferable for the hydrogenation gas used to be pure hydrogen.

The novel hydrogenation may be carried out in the presence or absence of a solvent or of a diluent. It is therefore not necessary to carry out the hydrogenation in solution.

However, it is preferable to use a solvent or diluent. The solvents or diluents used may be any suitable solvents or diluents. Their selection is not critical, so long as the solvent or diluent used is capable of forming a homogeneous solution with the benzenedicarboxylic ester(s) to be hydrogenated. The solvent or diluent may, for example, also comprise water.

Examples of suitable solvents or diluents include the following:

Straight-chain or cyclic ethers, such as tetrahydrofuran or dioxane, and also aliphatic alcohols where the alkyl radical preferably has from 1 to 10 carbon atoms, in particular from 3 to 6 carbon atoms.

Examples of alcohols whose use is preferred are isopropanol, n-butanol, isobutanol and n-hexanol.

It is also possible to use mixtures of these or of other solvents or diluents.

There is no particular limit on the amount used of the solvent or diluent, and this can be freely selected as required. However, preferred amounts are those which give a 10–70% strength by weight solution of the benzenedicarboxylic acid ester(s) intended for hydrogenation.

For the purposes of the novel process, it is particularly preferable for the product formed during the hydrogenation, i.e. the corresponding cyclohexane derivative, to be used as solvent, if desired alongside other solvents or diluents. In any case, some of the product formed in the process may be admixed with the benzenedicarboxylic acid derivative awaiting hydrogenation. Based on the weight of the compound intended for hydrogenation, it is preferable to admix from 1 to 30 times, particularly preferably from 5 to 20 times, in particular from 5 to 10 times, the amount of the reaction product as solvent or diluent.

The present invention also provides the use of the novel cyclohexane-1,3- or -1,4-dicarboxylic acid derivatives disclosed herein as plasticizers in plastics.

Compared with the phthalates mainly used as plasticizers hitherto, the cyclohexane-1,3- and -1,4-dicarboxylic acid esters used according to the invention have lower density and viscosity and give, inter alia, an improvement in low-temperature flexibility of the plastic over that obtained when using the corresponding phthalates as plasticizers, while properties such as Shore A hardness and mechanical properties of the resultant plastics are identical to those obtained when using phthalates. The cyclohexanepolycarboxylic acid (derivatives) used according to the invention moreover have a better processing performance in dry blends and therefore give increased production rates and also advantages in plastisol processes due to markedly lower viscosity compared with the corresponding phthalates.

New toxicological findings also make it clear that, in particular when compared with the phthalates and phthalate derivatives frequently used hitherto as plasticizers, the novel cyclohexane-1,3- and -1,4-dicarboxylic acid derivatives are not only suitable for use as plasticizers in respect of their physical and material properties but also advantageous from a toxicological point of view.

The phenomenon found with phthalates and mentioned at the outset, the formation of liver tumors in rodents, appears to be brought about by peroxisome-proliferator-activated receptor-α (PPARα). The peroxisome proliferation underlying this mechanism can be detected by various indicators, for example using the marked rise in absolute or relative liver weight, or using the rise in certain enzyme activities, such as the specific activity of the cyanide-insensitive palmitoyl-CoA oxidase (Pal-CoA oxidase).

It can be assumed that the novel cyclohexane-1,3- and -1,4-dicarboxylic acid derivatives, unlike various conventional plasticizers, in particular the phthalates and the phthalic acid derivatives often used for this purpose, do not bring about any biologically significant peroxisome proliferation and are therefore suitable for use as plasticizers in respect of their physical and material properties and are also considered as more advantageous than these conventional plasticizers from a toxicological point of view.

For the purposes of the present invention a compound is considered particularly toxicologically advantageous if experiments carried out on rodents which have been given a daily oral dose of 1000 mg/kg of body weight of this compound via a stomach tube for a period of at least 14 days show, in comparison with the corresponding untreated control animals, no statistically significant rise in the absolute liver weight or in the relative liver weight, i.e. of the liver weight based on the total body weight, and no toxicologically relevant rise in the specific enzyme activity of the cyanide-insensitive palmitoyl-CoA oxidase.

For the purposes of the present invention, a statistically significant rise in the absolute or relative liver weight is present in particular if the statistical rise in the absolute or relative liver weight of the experimental animal was determined by the Dunnett test as more than 10% over that of the untreated control animal (Dunnett, C. W. (1955), A multiple comparison procedure for comparing several treatments with a control, J. Am. Stat. Assoc. 50, 1096–1121; Dunnett, C. W. (1964), New tables for multiple comparisons with a control, Biometrics, 20, 482–491).

A toxicologically relevant rise in the specific activity of the cyanide-insensitive palmitoyl-CoA oxidase is present if the specific activity of the cyanide-insensitive palmitoyl-CoA oxidase, measured in the liver homogenate of an experimental animal which has received a daily oral dose of 1000 mg of test substance per kg of body weight via a stomach tube for a period of at least 14 days, is more than twice as high as the specific activity of the cyanide-insensitive palmitoyl-CoA oxidase determined in the liver homogenate of an untreated control animal.

The specific activity [mU/mg of protein] of the cyanide-insensitive palmitoyl-CoA oxidase is usually determined by the method of Lazarow (1981), Enzymology 72, 315–319, and the amount of protein in the liver homogenate is routinely determined by the protein-determination methods well known to the skilled worker, such as the Lowry method.

In the case of the novel cyclohexane-1,3- and -1,4-dicarboxylic acid esters disclosed here which are toxicologically advantageous in the sense of the present invention it is, furthermore, to be expected that relevant improvements will also be achieved in respect of reproduction-toxicology parameters in comparison with conventional plasticizers, in particular with the phthalates and phthalic acid derivatives often used for this purpose.

The present invention therefore in particular provides the use, as a plasticizer for preparing toxicologically advantageous plastics, of a novel cyclohexane-1,3- or -1,4-dicarboxylic acid derivative disclosed herein or of a mixture made from two or more of these which, when tested on rodents at a daily oral dose of 1000 mg/kg of body weight of the appropriate cyclohexane-1,3- or -1,4-dicarboxylic acid derivative or of a mixture made from two or more of these, via a stomach tube, over a period of at least 14 days, gives no significant rise in the liver weight after the treatment and does not give a doubling of the specific activity, measured in the liver homogenate, of the cyanide-insensitive palmitoyl-CoA oxidase when comparison is made with untreated control animals.

The novel process will now be described below in greater detail, using some examples.

EXAMPLES

Example 1

Preparation Example

A meso/macroporous aluminum oxide support in the form of 4 mm extrudates and having a BET surface area of 238 $m^2/g$ and a pore volume of 0.45 ml/g was saturated with an aqueous ruthenium(III) nitrate solution of concentration 0.8% by weight. 0.15 ml/g (about 33% of the total volume) of the pores of the support had a diameter of from 50 to 10,000 nm, and 0.30 ml/g (about 67% of the total pore volume) of the pores of the support had a pore diameter of from 2 to 50 nm. The volume of solution absorbed here by the support was approximately equal to the pore volume of the support used.

The support saturated with ruthenium(III) nitrate solution was then dried at 120° C. and activated (reduced) at 200° C. in a stream of hydrogen. The resultant catalyst comprised 0.05% by weight of ruthenium, based on the weight of the catalyst.

Example 2

Hydrogenation of di(2-ethylhexyl) terephthalate 40 g of the supported Ru catalyst as in the preparation example were charged to a 1.21 pressure reactor in a catalyst basket insert and mixed with 610 g (1.56 mol) of di(2-ethylhexyl) terephthalate. The hydrogenation was carried out with pure hydrogen at a constant pressure of 200 bar at 140° C. The hydrogenation was continued until no more hydrogen was absorbed (3.5 h) and the pressure in the reactor was then reduced. The conversion of di(2-ethylhexyl) terephthalate was 99.8%. The yield of the corresponding hydrogenation product cyclohexane-1,4-dicarboxylic acid di(2-ethylhexyl) ester was 97%, based on the total amount of di(2-ethylhexyl) terephthalate used.

TABLE 1

Starting materials for preparing the novel cyclohexane-1,3-dicarboxylic acid esters:

| Starting material | CAS No. of the starting material |
|---|---|
| diisobutyl isophthalate [bis(2-methylpropyl) isophthalate] | 1528-64-9 |
| di-n-pentyl isophthalate | 4654-16-4 |
| di(1-methylbutyl)isophthalate | 75151-01-8 |
| di-n-heptyl isophthalate | 4654-17-5 |
| diisooctyl isophthalate | 71850-11-8 |
| dinonyl isophthalate | 4654-19-7 |
| diisodecyl isophthalate | 52284-35-2 |
| diundecyl isophthalate | 18699-46-2 |
| di-n-dodecyl isophthalate | 18699-47-3 |
| bis(1-methylpropyl) isophthalate | 75150-99-1 |
| bis(1,1-dimethylpropyl) isophthalate | 117769-95-6 |
| bis(2-methylbutyl) isophthalate | 75151-03-0 |
| bis(3-methylbutyl) isophthalate | 1528-63-8 |
| bis(1-ethyl-2-methylpropyl) isophthalate | 166391-29-3 |

TABLE 1-continued

Starting materials for preparing the novel cyclohexane-1,3-dicarboxylic acid esters:

| Starting material | CAS No. of the starting material |
|---|---|
| bis(1-ethylbutyl) isophthalate | 166391-28-2 |
| bis(1,2,2-trimethylpropyl) isophthalate | 166391-27-1 |
| bis(2-ethylbutyl) isophthalate | 166391-25-9 |
| bis(4-methylpentyl) isophthalate | 159375-22-1 |
| bis(1,3-dimethylbutyl) isophthalate | 166391-26-0 |
| bis(1,1-diethylpropyl) isophthalate | 123095-15-8 |
| bis(1-ethyl-1-methylpropyl) isophthalate | 145530-74-1 |
| bis[2-methyl-1-(1-methylethyl)propyl] isophthalate | 166391-48-6 |
| bis(2,2-dimethylhexyl) isophthalate | 17673-11-9 |
| bis[3-methyl-1-(2-methylpropyl)butyl] isophthalate | 127474-92-4 |
| bis(3,3,5-trimethylhexyl) isophthalate | 208527-97-3 |
| bis(2-ethyl-1,1-dimethylhexyl) isophthalate | 123892-24-0 |
| 1-heptyl-3-hexyl isophthalate | 166391-30-6 |
| 1-[2-ethylbutyl]-3-heptyl isophthalate | 166391-41-9 |
| 1-heptyl-3-[1,2,2-trimethylpropyl] isophthalate | 166391-43-1 |
| 1-dimethylbutyl-3-heptyl isophthalate | 166391-42-0 |
| 1-[1-ethylbutyl]-3-heptyl isophthalate | 166391-44-2 |
| 1-[1-ethyl-2-methylpropyl]-3-heptyl isophthalate | 166391-45-3 |
| 1-decyl-3-hexyl isophthalate | 154064-19-4 |
| 1-hexyl-3-[2-methyl-1-(1-methylethyl)propyl] isophthalate | 166391-46-4 |
| 1-dodecyl-3-hexyl isophthalate | 154147-75-8 |
| 1-nonyl-3-octyl isophthalate | 154147-74-7 |

TABLE 2

Starting materials for preparing the novel cyclohexane-1,4-dicarboxylic acid esters:

| Starting material | CAS No. of the starting material |
|---|---|
| diisobutyl terephthalate [bis(2-methylpropyl) terephthalate] | 18699-48-4 |
| di-n-pentyl terephthalate | 1818-95-7 |
| bis(1-methylbutyl) terephthalate | 75151-02-9 |
| di-n-heptyl terephthalate | 4654-25-5 |
| diisooctyl terephthalate | 27937-24-2 |
| dinonyl terephthalate | 4564-27-7 |
| diisononyl terephthalate | 59802-05-0 |
| diisodecyl terephthalate | 52174-72-8 |
| diundecyl terephthalate | 111204-04-7 |
| di-n-dodecyl terephthalate | 18749-84-3 |
| bis(1-methylpropyl) terephthalate | 64445-74-5 |
| bis(1,1-dimethylpropyl) terephthalate | 117769-96-7 |
| bis(2-methylbutyl) terephthalate | 75151-04-1 |
| bis(3-methylbutyl) terephthalate | 18699-49-5 |
| bis(1-ethylbutyl) terephthalate | 166391-32-8 |
| bis(4-methylpentyl) terephthalate | 159375-21-0 |
| bis[2-methyl-1-(1-methylethyl)propyl] terephthalate | 166391-33-9 |
| 2-methyl-bis(2-ethylhexyl) terephthalate | 51248-91-0 |
| bis(1-methylheptyl) terephthalate | 87321-19-5 |
| bis(2-ethyl-4-methylpentyl) terephthalate | 59726-62-4 |
| bis(2-methylheptyl) terephthalate | 83789-07-5 |
| bis(1,1,3,3-tetramethylbutyl) terephthalate | 90062-57-0 |
| bis(7-methyloctyl) terephthalate | 129951-42-4 |
| bis(8-methylnonyl) terephthalate | 129951-40-2 |
| 1-[8-methylnonyl]-4-octyl terephthalate | 129951-39-9 |
| 1-decyl-4-octyl terephthalate | 129951-41-3 |

We claim:
1. A cyclohexane-1,3- or -1,4-dicarboxylic acid ester selected from the group consisting of
cyclohexane-1,3-dicarboxylic acid dinonyl ester;
cyclohexane-1,3-dicarboxylic acid diisodecyl ester;
cyclohexane-1,3-dicarboxylic acid diundecyl ester;
cyclohexane-1,3-dicarboxylic acid didodecyl ester;
cyclohexane-1,3-dicarboxylic acid bis(1-ethyl-2-methylpropyl) ester;

cyclohexane-1,3-dicarboxylic acid bis(1-ethylbutyl) ester;
cyclohexane-1,3-dicarboxylic acid bis(1,2,2-trimethylpropyl) ester;
cyclohexane-1,3-dicarboxylic acid bis(2-ethylbutyl) ester;
cyclohexane-1,3-dicarboxylic acid bis(4-methylpentyl) ester;
cyclohexane-1,3-dicarboxylic acid bis(1,3-dimethylbutyl) ester;
cyclohexane-1,3-dicarboxylic acid bis(1,1-diethylpropyl) ester;
cyclohexane-1,3-dicarboxylic acid bis(1-ethyl-1-methylpropyl) ester;
cyclohexane-1,3-dicarboxylic acid bis[2-methyl-1-(1-methylethyl)propyl] ester;
cyclohexane-1,3-dicarboxylic acid bis(2,2-dimethylhexyl) ester;
cyclohexane-1,3-dicarboxylic acid bis[3-methyl-1-(2-methylpropyl)butyl] ester;
cyclohexane-1,3-dicarboxylic acid bis(3,3,5-trimethylhexyl) ester;
cyclohexane-1,3-dicarboxylic acid bis(2-ethyl-1,1-dimethylhexyl) ester;
cyclohexane-1,3-dicarboxylic acid 1-heptyl-3-hexyl ester;
cyclohexane-1,3-dicarboxylic acid 1-[2-ethylbutyl]-3-heptyl ester;
cyclohexane-1,3-dicarboxylic acid 1-heptyl-3-[1,2,2-trimethylpropyl] ester;
cyclohexane-1,3-dicarboxylic acid 1-dimethylbutyl-3-heptyl ester;
cyclohexane-1,3-dicarboxylic acid 1-[1-ethylbutyl]-3-heptyl ester;
cyclohexane-1,3-dicarboxylic acid 1-[1-ethyl-2-methylpropyl]-3-heptyl ester;
cyclohexane-1,3-dicarboxylic acid 1-decyl-3-hexyl ester;
cyclohexane-1,3-dicarboxylic acid 1-hexyl-3-[2-methyl-1-(1-methylethyl)propyl] ester;
cyclohexane-1,3-dicarboxylic acid 1-dodecyl-3-hexyl ester;
cyclohexane-1,3-dicarboxylic acid 1-nonyl-3-octyl ester;
cyclohexane-1,4-dicarboxylic acid diisobutyl ester;
cyclohexane-1,4-dicarboxylic acid dipentyl ester;
cyclohexane-1,4-dicarboxylic acid bis(1-methylbutyl) ester;
cyclohexane-1,4-dicarboxylic acid diheptyl ester;
cyclohexane-1,4-dicarboxylic acid diisooctyl ester;
cyclohexane-1,4-dicarboxylic acid dinonyl ester;
cyclohexane-1,4-dicarboxylic acid diisononyl ester;
cyclohexane-1,4-dicarboxylic acid diundecyl ester;
cyclohexane-1,4-dicarboxylic acid didodecyl ester;
cyclohexane-1,4-dicarboxylic acid bis(1-methylpropyl) ester;
cyclohexane-1,4-dicarboxylic acid bis(1,1-dimethylpropyl) ester;
cyclohexane-1,4-dicarboxylic acid bis(2-methylbutyl) ester;
cyclohexane-1,4-dicarboxylic acid bis(3-methylbutyl) ester;
cyclohexane-1,4-dicarboxylic acid bis(1-ethylbutyl) ester;
cyclohexane-1,4-dicarboxylic acid bis(4-methylpentyl) ester;
cyclohexane-1,4-dicarboxylic acid bis[2-methyl-1-(1-methylethyl)propyl] ester;
2-methylcyclohexane-1,4-dicarboxylic acid bis(2-ethylhexyl) ester;
cyclohexane-1,4-dicarboxylic acid bis(1-methylheptyl) ester;
cyclohexane-1,4-dicarboxylic acid bis(2-ethyl-4-methylpentyl) ester;
cyclohexane-1,4-dicarboxylic acid bis(2-methylheptyl) ester;
cyclohexane-1,4-dicarboxylic acid bis(1,1,3,3-tetramethylbutyl) ester;
cyclohexane-1,4-dicarboxylic acid bis(7-methyloctyl) ester;
the cyclohexane-1,4-dicarboxylic acid bis(8-methylnonyl) ester;
cyclohexane-1,4-dicarboxylic acid 1-[8-methylnonyl]-4-octyl ester;
cyclohexane-1,4-dicarboxylic acid 1-decyl-4-octyl ester.

2. A process for producing a cyclohexane-1,3- or -1,4-dicarboxylic acid ester or mixtures thereof by hydrogenating an isophthalic or terephthalic ester selected from the group consisting of
diheptyl isophthalate with CAS No. 4654-17-5;
diisooctyl isophthalate with CAS No. 71850-11-8;
dinonyl isophthalate with CAS No. 4654-19-7;
diisodecyl isophthalate with CAS No. 52284-35-2;
diundecyl isophthalate with CAS No. 18699-46-2;
didodecyl isophthalate with CAS No. 18699-47-3;
bis(1-ethyl-2-methylpropyl) isophthalate with CAS No. 16639391-29-3;
bis(1-ethylbutyl) isophthalate with CAS No. 166391-28-2;
bis(1,2,2-trimethylpropyl) isophthalide with CAS No. 166391-27-1;
bis(2-ethylbutyl) isophthalate with CAS No. 166391-25-9;
bis(4-methylpentyl) isophthalate with CAS No. 159375-22-1;
bis(1,3-dimethylbutyl) isophthalate with CAS No. 166391-26-0;
bis(1,1-diethylpropyl) isophthalate with CAS No. 123095-15-8;
bis(1-ethyl-1-methylpropyl) isophthalate with CAS No. 145530-74-1;
bis[2-methyl-1-(1-methylethyl)propyl] isophthalate with CAS No. 166391-48-6;
bis(2,2-dimethylhexyl) isophthalate with CAS No. 17673-11-9;
bis[3-methyl-1-(2-methylpropyl)butyl] isophthalate with CAS No. 127474-92-4;
bis(3,3,5-trimethylhexyl) isophthalate with CAS No. 208527-97-3;
bis(2-ethyl-1,1-dimethylhexyl) isophthalate with CAS No. 123892-24-0;
1-heptyl-3-hexyl isophthalate with CAS No. 166391-30-6;
1-[2-ethylbutyl]-3-heptyl isophthalate with CAS No. 166391-41-9;
1-heptyl-3-[1,2,2-trimethylpropyl] isophthalate with CAS No. 166391-43-1;
1-dimethylbutyl-3-heptyl isophthalate with CAS No. 166391-42-0;
1-[1-ethylbutyl]-3-heptyl isophthalate with CAS No. 166391-44-2;
1-[1-ethyl-2-methylpropyl]-3-heptyl isophthalate with CAS No. 166391-45-3;
1-decyl-3-hexyl isophthalate with CAS No. 154064-19-4;

1-hexyl-3-[2-methyl-1-(1-methylethyl)propyl] isophthalate with CAS No. 166391-46-4;
1-dodecyl-3-hexyl isophthalate with CAS No. 154147-75-8;
1-nonyl-3-octyl isophthalate with CAS No. 154147-74-7;
diisobutyl terephthalate with Chemical Abstracts Registry number 18699-48-4;
dipentyl terephthalate with CAS No. 1818-95-7;
bis(1-methylbutyl) terephthalate with CAS No. 75151-02-9;
diheptyl terephthalate with CAS No. 4654-25-5;
diisooctyl terephthalate with CAS No. 27937-24-2;
dinonyl terephthalate with CAS No. 4654-27-7;
diisononyl terephthalate with CAS No. 59802-05-0;
diisodecyl terephthalate with CAS No. 52114-72-8;
diundecyl terephthalate with CAS No. 111204-04-7;
didodecyl terephthalate with CAS No. 18749-84-3;
bis(1-methylpropyl) terephthalate with CAS No. 64445-74-5;
bis(1,1-dimethylpropyl) terephthalate with CAS No. 117769-96-7;
bis(2-methylbutyl) terephthalate with CAS No. 75151-04-1;
bis(3-methylbutyl) terephthalate with CAS No. 18699-49-5;
bis(1-ethylbutyl) terephthalate with CAS No. 166391-32-8;
bis(4-methylpentyl) terephthalate with CAS No. 159375-21-0;
bis[2-methyl-1-(1-methylethyl)propyl] terephthalate with CAS No. 166391-33-9;
bis(2-ethylhexyl) 2-methylterephthalate with CAS No. 51248-916;
bis(1-methylheptyl) terephthalate with CAS No. 87321-19.5;
bis(2-ethyl-4-methylpentyl) terephthalate with CAS No. 59726-62-4;
bis(2-methylheptyl) terephthalate with CAS No. 83789-07-5;
bis(1,1,3,3-tetramethylbutyl) terephthalate with CAS No. 90062-47-0;
bis(7-methyloctyl) terephthalate with CAS No. 129951-1-42-4;
bis(8-methylnonyl) terephthalate with CAS No. 129951-40-2;
1-[8-methylnonyl]-4-octyl terephthalate with CAS No. 129951-39-9;
1-decyl-4-octyl terephthalate with CAS No. 129951-41-3;
or mixtures thereof by bringing one or more of said isophthalic or terephthalic esters into contact with a hydrogen-containing gas in the presence of a catalyst which comprises, as active metal, ruthenium applied to a support, said support having macro-pores.

3. A process as claimed in claim 2, wherein the support comprises activated carbon, silicon carbide, aluminum oxide, silicon dioxide, titanium dioxide, zirconium dioxide, magnesium oxide, zinc oxide or a mixture thereof.

4. A process as claimed in claim 2, wherein the hydrogenation is carried out in the presence of a solvent or diluent.

5. A process as claimed in claim 2, wherein the hydrogenation is carried out continuously.

6. A method for imparting flexibility, workability or stretchability to a plastic composition, said method comprising adding to the composition a cyclohexane-1,3- or 1,4-dicarboxylic acid ester selected from the group consisting of
cyclohexane-1,3-dicarboxylic acid dinonyl ester;
cyclohexane-1,3-dicarboxylic acid diisodecyl ester;
cyclohexane-1,3-dicarboxylic acid diundecyl ester;
cyclohexane-1,3-dicarboxylic acid didodecyl ester;
cyclohexane-1,3-dicarboxylic acid bis(1-ethyl-2-methylpropyl) ester;
cyclohexane-1,3-dicarboxylic acid bis(1-ethylbutyl) ester;
cyclohexane-1,3-dicarboxylic acid bis(1,2,2-trimethylpropyl) ester;
cyclohexane-1,3-dicarboxylic acid bis(2-ethylbutyl) ester;
cyclohexane-1,3-dicarboxylic acid bis(4-methylpentyl) ester;
cyclohexane-1,3-dicarboxylic acid bis(1,3-dimethylbutyl) ester;
cyclohexane-1,3-dicarboxylic acid bis(1,1-diethylpropyl) ester;
cyclohexane-1,3-dicarboxylic acid bis(1-ethyl-1-methylpropyl) ester;
cyclohexane-1,3-dicarboxylic acid bis[2-methyl-1-(1-methylethyl)propyl] ester;
cyclohexane-1,3-dicarboxylic acid bis(2,2-dimethylhexyl) ester;
cyclohexane-1,3-dicarboxylic acid bis[3-methyl-1-(2-methylpropyl)butyl] ester;
cyclohexane-1,3-dicarboxylic acid bis(3,3,5-trimethylhexyl) ester;
cyclohexane-1,3-dicarboxylic acid bis(2-ethyl-1,1-dimethylhexyl) ester;
cyclohexane-1,3-dicarboxylic acid 1-heptyl-3-hexyl ester
cyclohexane-1,3-dicarboxylic acid 1-[2-ethylbutyl]-3-heptyl ester;
cyclohexane-1,3-dicarboxylic acid 1-heptyl-3-[1,2,2-trimethylpropyl] ester;
cyclohexane-1,3-dicarboxylic acid 1-dimethylbutyl-3-heptyl ester;
cyclohexane-1,3-dicarboxylic acid 1-[1-ethylbutyl]-3-heptyl ester;
cyclohexane-1,3-dicarboxylic acid 1-[1-ethyl-2-methylpropyl]-3-heptyl ester;
cyclohexane-1,3-dicarboxylic acid 1-decyl-3-hexyl ester;
cyclohexane-1,3-dicarboxylic acid 1-hexyl-3-[2-methyl-1-(1-methylethyl)propyl] ester;
cyclohexane-1,3-dicarboxylic acid 1-dodecyl-3-hexyl ester;
cyclohexane-1,3-dicarboxylic acid 1-nonyl-3-octyl ester;
cyclohexane-1,4-dicarboxylic acid diisobutyl ester;
cyclohexane-1,4-dicarboxylic acid dipentyl ester;
cyclohexane-1,4-dicarboxylic acid bis(1-methylbutyl) ester;
cyclohexane-1,4-dicarboxylic acid diheptyl ester;
cyclohexane-1,4-dicarboxylic acid diisooctyl ester;
cyclohexane-1,4-dicarboxylic acid dinonyl ester;
cyclohexane-1,4-dicarboxylic acid diisononyl ester;
cyclohexane-1,4-dicarboxylic acid diisodecyl ester;
cyclohexane-1,4-dicarboxylic acid diundecyl ester;
cyclohexane-1,4-dicarboxylic acid didodecyl ester;
cyclohexane-1,4-dicarboxylic acid bis(1-methylpropyl) ester;
cyclohexane-1,4-dicarboxylic acid bis(1,1-dimethylpropyl) ester;
cyclohexane-1,4-dicarboxylic acid bis(2-methylbutyl) ester;
cyclohexane-1,4-dicarboxylic acid bis(3-methylbutyl) ester;
cyclohexane-1,4-dicarboxylic acid bis(1-ethylbutyl) ester;

cyclohexane-1,4-dicarboxylic acid bis(4-methylpentyl) ester;
cyclohexane-1,4-dicarboxylic acid bis[2-methyl-1-(1-methylethyl)propyl] ester;
cyclohexane-1,4-dicarboxylic acid bis(2-ethylhexyl) ester;
cyclohexane-1,4-dicarboxylic acid bis(1-methylheptyl) ester;
cyclohexane-1,4-dicarboxylic acid bis(2-ethyl-4-methylpentyl) ester;
cyclohexane-1,4-dicarboxylic acid bis(2-methylheptyl) ester;
cyclohexane-1,4-dicarboxylic acid bis(1,1,3,3-tetramethylbutyl) ester;
cyclohexane-1,4-dicarboxylic acid bis(7-methyloctyl) ester;
the cyclohexane-1,4-dicarboxylic acid bis(8-methylnonyl) ester;
cyclohexane-1,4-dicarboxylic acid 1-[8-methylnonyl]-4-octyl ester;
cyclohexane-1,4-dicarboxylic acid 1-decyl-4-octyl ester.

7. A method for testing or screening a cyclohexane-1,3- or -1,4-dicarboxylic acid ester or mixture thereof as claimed claim 1, said method comprising treating rodents at a daily oral dose of 1000 mg/kg of body weight with said cyclohexane-1,3- or -1,4-dicarboxylic acid ester or mixture thereof, via a stomach tube, over a period of at least 14 days, subsequently
measuring liver weight of said rodents and determining whether said weight has risen significantly, and
measuring specific activity, in the liver homogenate, of the cyanide-insensitive palmitoyl-CoA oxidase and determining whether said activity doubles when comparison is made with untreated control animals.

8. A process as claimed in claim 2, wherein the catalyst comprises, as active metal, ruthenium applied to a support, where the support has an average pore diameter of at least 50 nm and a BET surface area of not mom than 30 m$^2$/g and the amount of the active metal is from 0.01 to 30% by weight, based on the total weight of the catalyst.

9. A process as claimed in claim 8, wherein the support comprises activated carbon, silicon carbide, aluminum oxide, silicon dioxide, titanium dioxide, zirconium dioxide, magnesium oxide, zinc oxide or a mixture thereof.

10. A process as claimed in claim 8, wherein the hydrogenation is carried out in the presence of a solvent or diluent.

11. A process as claimed in claim 8, wherein the hydrogenation is carried out continuously.

12. A process as claimed in claim claim 2, wherein the catalyst comprises, as active metal, from 0.01 to 30% by weight, based on the total weight of the catalyst, of ruthenium applied to a support, where from 10 to 50% of the pore volume of the support formed by macropores with a pore diameter of from 50 to 10,000 nm and from 50 to 90% of the pore volume of the support is formed by mesopores with a pore diameter of from 2 to 50 nm.

13. A process as claimed in claim 12, wherein the support comprises activated carbon, silicon carbide, aluminum oxide, silicon dioxide, titanium dioxide, zirconium dioxide, magnesium oxide, zinc oxide or a mixture thereof.

14. A process as claimed in claim 12, wherein the hydrogenation is carried out in the presence of a solvent or diluent.

15. A process as claimed in claim 12, wherein the hydrogenation is carried out continuously.

16. A process as claimed in claim 2, wherein the catalyst comprises, as active metal, from 0.01 to 30% by weight, based on the total weight of the catalyst, of ruthenium applied to a support, where the support has an average pore diameter of at least 0.1 μm and a BET surface area of not more than 15 m$^2$/g.

17. A process as claimed in claim 16, wherein the support comprises activated carbon, silicon carbide, aluminum oxide, silicon dioxide, titanium dioxide, zirconium dioxide, magnesium oxide, zinc oxide or a mixture thereof.

18. A process as claimed in claim 16, wherein the hydrogenation is carried out in the presence of a solvent or diluent.

19. A process as claimed in claim 16, wherein the hydrogenation is carried out continuously.

20. The cyclohexane-1,3- or -1,4-dicarboxylic acid ester of claim 1, wherein the cyclohexane-1,3- or -1,4-dicarboxylic acid ester is selected from the group consisting of
cyclohexane-1,3-dicarboxylic acid dinonyl ester;
cyclohexane-1,3-dicarboxylic acid diundecyl ester;
cyclohexane-1,3-dicarboxylic acid didodecyl ester;
cyclohexane-1,3-dicarboxylic acid bis(1-ethyl-2-methylpropyl) ester;
cyclohexane-1,3-dicarboxylic acid bis(1-ethylbutyl) ester;
cyclohexane-1,3-dicarboxylic acid bis(1,2,2-trimethylpropyl) ester;
cyclohexane-1,3-dicarboxylic acid bis(2-ethylbutyl) ester;
cyclohexane-1,3-dicarboxylic acid bis(4-methylpentyl) ester;
cyclohexane-1,3-dicarboxylic acid bis(1,3-dimethylbutyl) ester;
cyclohexane-1,3-dicarboxylic acid bis(1,1-diethyl propyl) ester;
cyclohexane-1,3-dicarboxylic acid bis(1-ethyl-2-methylpropyl) ester;
cyclohexane-1,3-dicarboxylic acid bis(2-methyl-1-(1-methylethyl)propyl ester;
cyclohexane-1,3-dicarboxylic acid bis(2,2-dimethylhexyl) ester;
cyclohexane-1,3-dicarboxylic acid bis[3-methyl-1-(2-methylpropyl)butyl]ester;
cyclohexane-1,3-dicarboxylic acid bis(3,3,5-trimethylhexyl) ester;
cyclohexane-1,3-dicarboxylic acid bis(2-ethyl-1,1-dimethylhexyl) ester;
cyclohexane-1,3-dicarboxylic acid 1-heptyl-3-hexyl ester;
cyclohexane-1,3-dicarboxylic acid 1-[2-ethylbutyl]-3-heptyl ester;
cyclohexane-1,3-dicarboxylic acid 1-heptyl-3-[1,2,2-trimethylpropyl]ester;
cyclohexane-1,3-dicarboxylic acid 1-dimethylbutyl-3-heptyl ester;
cyclohexane-1,3-dicarboxylic acid 1-[1-ethylbutyl]-3-heptyl ester;
cyclohexane-1,3-dicarboxylic acid 1-[1-ethyl-2-methylpropyl]-3-heptyl ester;
cyclohexane-1,3-dicarboxylic acid 1-decyl-3-hexyl ester;
cyclohexane-1,3-dicarboxylic acid 1-heyl-3-[2-methyl-1-(1-methylethyl)propyl] ester;
cyclohexane-1,3-dicarboxylic acid 1-dodecyl-3-hexyl ester;
cyclohexane-1,3-dicarboxylic acid 1-nonyl-3-octyl ester;
cyclohexane-1,4-dicarboxylic acid diisobutyl ester;
cyclohexane-1,4-dicarboxylic acid dipentyl ester;
cyclohexane-1,4-dicarboxylic acid bis(1-methylbutyl) ester;
cyclohexane-1,4-dicarboxylic acid diheptyl ester;
cyclohexane-1,4-dicarboxylic acid didodecyl ester;

cyclohexane-1,4-dicarboxylic acid bis(1-methylpropyl) ester;
cyclohexane-1,4-dicarboxylic acid bis(1,1-dimethylpropyl) ester;
cyclohexane-1,4-dicarboxylic acid bis(2-methylbutyl) ester;
cyclohexane-1,4-dicarboxylic acid bis(3-methylbutyl) ester;
cyclohexane-1,4-dicarboxylic acid bis(1-ethylbutyl) ester;
cyclohexane-1,4-dicarboxylic acid bis(4-methylpentyl) ester;
cyclohexane-1,4-dicarboxylic acid bis[2-methyl-1-(1-methylethyl)propyl] ester;
2-methylcyclohexane-1,4-dicarboxylic acid bis(2-ethylhexyl) ester;
cyclohexane-1,4-dicarboxylic acid bis(1-methylheptyl) ester;
cyclohexane-1,4-dicarboxylic acid bis(2-ethyl-4-methylpentyl) ester;
cyclohexane-1,4-dicarboxylic acid bis(2-methylheptyl) ester;
cyclohexane-1,4-dicarboxylic acid bis(1,1,3,3-tetramethylbutyl) ester;
cyclohexane-1,4-dicarboxylic acid bis(7-methyloctyl) ester;
the cyclohexane-1,4-dicarboxylic acid bis(8-methylnonlyl) ester;
cyclohexane-1,4-dicarboxylic acid 1-[8-methylnonyl]-4-octyl ester;
cyclohexane-1,4-dicarboxylic acid 1-decyl-4-octyl ester.

21. The method of claim 6, wherein the plastic composition is maintained substantially free of phthalates.

22. A plastic composition comprising a cyclohexane-1,3- or 1,4-dicarboxylic acid ester selected from the group consisting of
cyclohexane-1,3-dicarboxylic acid dinonyl ester;
cyclohexane-1,3-dicarboxylic acid diusooctyl ester;
cyclohexane-1,3-dicarboxylic acid diundecyl ester;
cyclohexane-1,3-dicarboxylic acid didodecyl ester;
cyclohexane-1,3-dicarboxylic acid bis(1-ethyl-2-methylpropyl) ester;
cyclohexane-1,3-dicarboxylic acid bis(1-ethylbutyl ester;
cyclohexane-1,3-dicarboxylic acid bis(1,2,2-trimethylpropyl) ester;
cyclohexane-1,3-dicarboxylic acid bis(2-ethylbutyl) ester;
cyclohexane-1,3-dicarboxylic acid bis(4-methylpentyl) ester;
cyclohexane-1,3-dicarboxylic acid bis(1,3-dimethylbutyl) ester;
cyclohexane-1,3-dicarboxylic acid bis(1,1-diethylpropyl) ester;
cyclohexane-1,3-dicarboxylic acid bis(1-ethyl-1-methylpropyl) ester;
cyclohexane-1,3-dicarboxylic acid bis[2-methyl-1-(1-methylethyl)propyl] ester;
cyclohexane-1,3-dicarboxylic acid bis(2,2-dimethylhexyl) ester;
cyclohexane-1,3-dicarboxylic acid bis[3-methyl-1-(2-methylpropyl)butyl] ester;
cyclohexane-1,3-dicarboxylic acid bis(3,3,5-trimethylhexyl) ester;
cyclohexane-1,3-dicarboxylic acid bis(2-ethyl-1,1-dimethylhexyl) ester;
cyclohexane-1,3-dicarboxylic acid 1-heptyl-3-hexyl ester;
cyclohexane-1,3-dicarboxylic acid 1-[2-ethylbutyl]-3-heptyl ester;
cyclohexane-1,3-dicarboxylic acid 1-heptyl-3-[1,2,2-trimethylpropyl] ester;
cyclohexane-1,3-dicarboxylic acid 1-dimethylbityl-3-heptyl ester;
cyclohexane-1,3-dicarboxylic acid 1-[1-ethylbutyl]-3-heptyl ester;
cyclohexane-1,3-dicarboxylic acid 1-[1-ethyl-2-methylpropyl]-3-heptyl ester;
cyclohexane-1,3-dicarboxylic acid 1-decyl-3-hexyl ester;
cyclohexane-1,3-dicarboxylic acid 1-hexyl-3-[2-methyl-1-(1-methylethyl)propyl] ester;
cyclohexane-1,3-dicarboxylic acid 1-dodecyl-3-hexyl ester;
cyclohexane-1,3-dicarboxylic acid 1-nonly-3-octyl ester;
cyclohexane-1,4-dicarboxylic acid diisobutyl ester;
cyclohexane-1,4-dicarboxylic acid dipentyl ester;
cyclohexane-1,4-dicarboxylic acid bis(1-methylbutyl) ester;
cyclohexane-1,4-dicarboxylic acid diheptyl ester;
cyclohexane-1,4-dicarboxylic acid diisooctyl ester;
cyclohexane-1,4-dicarboxylic acid dinonyl ester;
cyclohexane-1,4-dicarboxylic acid diisononyl ester;
cyclohexane-1,4-dicarboxylic acid diisodecyl ester;
cyclohexane-1,4-dicarboxylic acid diundecyl ester;
cyclohexane-1,4-dicarboxylic acid didodecyl ester;
cyclohexane-1,4-dicarboxylic acid bis(1-methylpropyl) ester;
cyclohexane-1,4-dicarboxylic acid bis(1,1-dimethylpropyl) ester;
cyclohexane-1,4-dicarboxylic acid bis(2-methylbutyl) ester;
cyclohexane-1,4-dicarboxylic acid bis(3-methylbutyl) ester;
cyclohexane-1,4-dicarboxylic acid bis(1-ethylbutyl) ester;
cyclohexane-1,4-dicarboxylic acid bis(4-methylpentyl) ester;
cyclohexane-1,4-dicarboxylic acid bis[2-methyl-1-(1-methylethyl)propyl] ester;
2-methylcyclohexane-1,4-dicarboxylic acid bis(2-ethylhexyl) ester;
cyclohexane-1,4-dicarboxylic acid bis(1-methylheptyl) ester;
cyclohexane-1,4-dicarboxylic acid bis(2-ethyl-4-methylpentyl) ester;
cyclohexane-1,4-dicarboxylic acid bis(2-methylheptyl) ester;
cyclohexane-1,4-dicarboxylic acid bis(1,1,3,3-tetramethylbutyl) ester;
cyclohexane-1,4-dicarboxylic acid bis(7-methyloctyl) ester;
the cyclohexane-1,4-dicarboxylic acid bis(8-methylnonyl) ester;
cyclohexane-1,4-dicarboxylic acid 1-[8-methylnonyl]-4-octyl ester;
cyclohexane-1,4-dicarboxylic acid 1-decyl-4-octyl ester.

23. The plastic composition of claim 22, wherein said composition is substantially free of phthalates.

24. The cyclohexane-1,3- or -1,4-dicarboxylic acid ester as claimed in claim 1, wherein the cyclohexane-1,4-dicarboxylic acid ester is selected from the group consisting of
cyclohexane-1,4-dicarboxylic acid diheptyl ester;
cyclohexane-1,4-dicarboxylic acid diisooctyl ester;
cyclohexane-1,4-dicarboxylic acid dinonyl ester;
cyclohexane-1,4-dicarboxylic acid diisononyl ester;

cyclohexane-1,4-dicarboxylic acid diundecyl ester;
cyclohexane-1,4-dicarboxylic acid didodecyl ester;
cyclohexane-1,4-dicarboxylic acid bis(1-ethylbutyl) ester;
cyclohexane-1,4-dicarboxylic acid bis(4-methylpentyl) ester;
cyclohexane-1,4-dicarboxylic acid bis[2-methyl-1-(1-methylethyl)propyl] ester;
2-methylcyclohexane-1,4-dicarboxylic acid bis(2-ethylhexyl) ester;
cyclohexane-1,4-dicarboxylic acid bis(1-methylheptyl) ester;
cyclohexane-1,4-dicarboxylic acid bis(2-ethyl-4-methylpentyl) ester;
cyclohexane-1,4-dicarboxylic acid bis(2-methylheptyl) ester;
cyclohexane-1,4-dicarboxylic acid bis(1,1,3,3-tetramethylbutyl) ester;
cyclohexane-1,4-dicarboxylic acid bis(7-methyloctyl) ester;
the cyclohexane-1,4-dicarboxylic acid bis(8-methylnonyl) ester;
cyclohexane-1,4-dicarboxylic acid 1-[8-methylnonyl]-4-octyl ester;
cyclohexane-1,4-dicarboxylic acid 1-decyl-4-octyl ester.

25. The cyclohexane-1,3- or -1,4-dicarboxylic acid ester of claim 1, wherein the cyclohexane-1,4-dicarboxylic acid ester is selected from the group consisting of
cyclohexane-1,4-dicarboxylic acid diheptyl ester;
cyclohexane-1,4-dicarboxylic acid didodecyl ester;
cyclohexane-1,4-dicarboxylic acid bis(1-ethylbutyl) ester;
cyclohexane-1,4-dicarboxylic acid bis(4-methylpentyl) ester;
cyclohexane-1,4-dicarboxylic acid bis[2-methyl-1-(1-methylethyl)propyl] ester;
2-methylcyclohexane-1,4-dicarboxylic acid bis(2-ethylhexyl) ester;
cyclohexane-1,4-dicarboxylic acid bis(1-methylheptyl) ester;
cyclohexane-1,4-dicarboxylic acid bis(2-ethyl-4-methylpentyl) ester;
cyclohexane-1,4-dicarboxylic acid bis(2-methylheptyl) ester;
cyclohexane-1,4-dicarboxylic acid bis(1,1,3,3-tetramethylbutyl) ester;
cyclohexane-1,4-dicarboxylic acid bis(7-methyloctyl) ester;
the cyclohexane-1,4-dicarboxylic acid bis(8-methylnonlyl) ester;
cyclohexane-1,4-dicarboxylic acid 1-[8-methylnonyl]-4-octyl ester;
cyclohexane-1,4-dicarboxylic acid 1-decyl-4-octyl ester.

* * * * *

UNITED STATES PATENT AND TRADEMARK OFFICE
CERTIFICATE OF CORRECTION

PATENT NO. : 7,208,545 B1
APPLICATION NO. : 09/959380
DATED : April 24, 2007
INVENTOR(S) : Brunner et al.

It is certified that error appears in the above-identified patent and that said Letters Patent is hereby corrected as shown below:

Claim 8, column 19, indicated line 38: "mom" should read --more--

Claim 20, column 20, indicated line 32: "bis(1-ethyl-2-methyl-" should read --bis(1-ethyl-1-methyl- --

Claim 22, column 22, indicated line 16: "nonly" should read --nonyl--

Signed and Sealed this

Third Day of July, 2007

JON W. DUDAS
*Director of the United States Patent and Trademark Office*